United States Patent [19]

Tomoi et al.

[11] Patent Number: 5,093,342
[45] Date of Patent: Mar. 3, 1992

[54] USE OF OMEPRAZOLE AS AN ANTIMICROBIAL AGENT

[75] Inventors: Masaaki Tomoi, Higashi-Osaka; Yoshifumi Ikeda, Nakatsu; Yoshiko Yokota, Ibaraki, all of Japan

[73] Assignee: Aktiebolaget Hassle, Molndal, Sweden

[21] Appl. No.: 572,951

[22] PCT Filed: Feb. 2, 1990

[86] PCT No.: PCT/SE90/00070

§ 371 Date: Sep. 12, 1990

§ 102(e) Date: Sep. 12, 1990

[87] PCT Pub. No.: WO90/09175

PCT Pub. Date: Aug. 23, 1990

[30] Foreign Application Priority Data

Feb. 9, 1989 [JP] Japan .................................. 1-30311

[51] Int. Cl.⁵ .............................................. A61K 31/44
[52] U.S. Cl. ................................................... 514/328
[58] Field of Search ......................................... 514/338

[56] References Cited

FOREIGN PATENT DOCUMENTS 0005129 4/1981 European Pat. Off. .
0045200 2/1982 European Pat. Off. .
0124495 1/1987 European Pat. Off. .
8600742 9/1986 Sweden .

*Primary Examiner*—Jerome D. Goldberg
*Attorney, Agent, or Firm*—White & Case

[57] ABSTRACT

Use of 5-methoxy-2[[(4-methoxy-3,5-dimethyl-2-pyridinyl)methyl]-sulfinyl]-1H-benzimidazole or a pharmaceutically acceptable salt thereof in the treatment of infectious diseases, especially such caused by Campylobacter pylori.

1 Claim, No Drawings

USE OF OMEPRAZOLE AS AN ANTIMICROBIAL AGENT

FIELD OF THE INVENTION

The present invention relates to the new use of 5-methoxy-2-[[(4-methoxy-3,5-dimethyl-2-pyridinyl)methyl]-sulfinyl]-1H-benzimidazole (generic name: omeprazole) or a salt thereof as an antimicrobial agent and more particularly as an antimicrobial agent, which is particularly active against gram-negative bacteria.

BACKGROUND OF THE INVENTION

In view of the abuse or unscrupulous use of antimicrobial drugs in the treatment of infectious diseases or for other purposes and the consequent emergence of drug-resistant strains, increased incidence of microbial substitution due to disturbance of the bacterial flora, changes in profile of infectious diseases, etc., there has been a constant demand for the development of new antimicrobial agents.

This application is especially directed to the treatment of infections caused by Campylobacter pylori. Campylobacter pylori is a gram-negative spirilliform bacterium which colonises deeply in the gastric mucosa. Treatment with commonly used antibiotics has given insufficient effect.

PRIOR ART

Omeprazole and its pharmaceutically acceptable salts, which are used in accordance with the invention, are known compounds, e.g. from EP 5129 and EP 124495 and can be produced by known processes, for example by the process described in Japanese Patent Application No. 34956/1985.

OUTLINE OF THE INVENTION

The intensive research undertaken by the inventors of the present invention for accomplishing the above-mentioned object revealed surprisingly that 5-methoxy-2-[[(4-methoxy-3,5-dimethyl-2-pyridinyl)methyl]-sulfinyl]-1H-benzimidazole (generic name: omeprazole) and pharmaceutically acceptable salts thereof, which are known to have gastric antisecretory activity known to be an antiulcer drug have excellent antimicrobial activity as well.

Heretofore, it has never been known that omeprazole or any compound analogous thereto has antimicrobial activity.

Predicated on the above finding, the present invention relates to an antimicrobial agent containing omeprazole or a salt thereof as an active ingredient.

The salt of omeprazole is virtually optional in kind but is preferably a pharmaceutically acceptable salt. Examples of such salts include inorganic salts, such as alkali metal salts, e.g. sodium salt, potassium salt etc., alkaline earth metal salts. e.g. calcium salt, magnesium salt etc., ammonium salt, organic salts such as organic amine salts, e.g. trimethylamine salt, triethylamine salt, pyridine salt, procaine acid, picoline salt, dicyclohexylamine salt, N,N-dibenzylethylenediamine salt, N-methylglucamine salt, diethanolamine salt, triethanolamine salt, tris(hydroxymethylamino)methane salt, phenylethylbenzylamine salt, dibenzylethylenediamine salt.

The antimicrobial agent according to the present invention is particularly active against gram-negative bacteria, especially microaerophilic bacteria, inter alia bacteria of the genus *Campylobacter* represented by *C. pylori*, and can be effectively utilized for the prevention and treatment of infectious diseases due to such bacteria in mammalian animals including man, cattle, horse, dog, mouse and rat, in the control and inhibition of environmental pollution, or as a disinfectant.

The antimicrobial agent according to the present invention can be made available in a pharmaceutical formulation comprising one or more active ingredients selected from the group consisting of omeprazole and salts thereof or in a formulation containing optional substances as additives (for example, a carrier).

For the treatment or prevention of bacterial infections, for instance, the antimicrobial agent of the invention is generally administered in the form of a pharmaceutical preparation containing omeprazole as such (i.e. the free base) or a salt thereof as an active ingredient in combination with a pharmaceutically acceptable carrier by the oral, rectal or parenteral route. The carrier mentioned above may be a solid, semi-solid or liquid diluent or a capsule. Compatible dosage forms include various types of tablets, capsules, granules, powders, oral liquids, injections and so on. The proportions of the active ingredient in the total composition is generally 0.1 to 100 weight percent and preferably 0.1 to 95 weight percent. In the case of an injectable preparation, the range of 0.1 to 20 weight percent is particularly preferred. In the case of a preparation for oral administration, the preferred proportion is 2 to 50 weight percent.

In the manufacture of a pharmaceutical preparation for oral administration, the active ingredient can be formulated with a solid particulate carrier such as lactose, sucrose, sorbitol, mannitol, starch, amylopectin, a cellulose derivative or gelatin, and a lubricating agent such as magnesium stearate, calcium stearate or polyethylene glycol wax may be further incorporated. The resulting composition is then compressed into tablets. Coated tablets or dragees can be manufactured by coating the core tablets, thus prepared, with a thick sugar solution containing gum arabic, gelatin, talc, titanium dioxide, etc. or a lacquor prepared using a volatile organic solvent or solvent mixture.

Soft gelatin capsules can be manufactured by filling a composition comprising the active ingredient and a known vegetable oil into capsules. Hard gelatin capsules can be manufactured by filling into capsules the granules or pellets each comprising the active ingredient and a solid particulate carrier such as lactose, sucrose, sorbitol, mannitol, potato starch, corn starch, amylopectin, a cellulose derivative or gelatin.

Preparations for rectal administration are preferably suppositories containing the active ingredient and a neutral oleaginous base, gelatin capsules for rectal administration which contain the active ingredient and a vegetal oil or paraffin oil, and rectal ointments.

Liquid preparations for oral administration can be syrups or suspensions, typically a solution containing 0.2 to 20 weight percent of the active ingredient with the balance being a mixture of sucrose with ethanol, water, glycerol and/or propylene glycol. Optionally, these preparations may additionally contain colors, corrigents, saccharin and, as a thickener, carboxymethylcellulose or the like. Injections can be manufactured in the form of aqueous solutions, typically an aqueous solution containing a pharmaceutically acceptable water-soluble salt of the active ingredient preferably in a concentration of 0.1 to 10 weight percent. These preparations may further contain a stabilizer and/or a buffer and may be provided in ampules containing various unit doses.

The dosage of omeprazole or a salt thereof depends on individual needs (for example, the patient's condition, body weight, age, sex, etc.) as well as on the method of administration. Generally speaking, the oral dosage may range from 1 to 400 mg as active ingredient per day per adult human and the intravenous dosage may range from 1 to 200 mg per day per adult human, and each may be administered in one to a few divided doses.

PHARMACOLOGICAL DATA

Experiment 1

The in vitro antimicrobial activity of the active ingredient of the present invention was assayed by the following agar plate dilution method.

A loopful ($10^7$ cells/ml) of the test strain cultured in Brucella Broth containing 5% of horse serum under 10% carbon dioxide gas for 2 days was inoculated onto Brucella Agar containing 5% horse lysed blood. This medium contained a varying concentration of omeprazole. The inoculated media were incubated at 37° C. under 10% carbon dioxide gas for 2 days and the minimal inhibitory concentration (MIC) was determined. The result is set forth in Table 1.

TABLE 1

| Test organism | MIC (μg/ml) |
|---|---|
| Campylobacter pylori 8005 | 0.39 |

EXAMPLES

The following examples are intended to illustrate the antimicrobial agent of the invention in further detail and should be no means be constructed as limiting the scope of the invention.

| Example 1 (25 mg tablets) | |
|---|---|
| Omeprazole | 250 g |
| Lactose | 175.8 g |
| Corn starch | 169.7 g |

The above ingredients are mixed and wetted with 10% gelatin solution, and the wet mixture is sieved through a 12-mesh screen and pulverized. The resulting powder is dried and magnesium stearate is added. This mixture is then compressed into tablets each containing 25 mg of omeprazole.

| Example 2 (capsules) | |
|---|---|
| Omeprazole | 93.5 weight % |
| Carboxymethylcellulose calcium | 3.7 weight % |
| Magnesium stearate | 1.9 weight % |
| Light silicic anhydride | 0.9 weight % |

The above ingredients are mixed thoroughly and filled into capsules.

| Example 3 (capsules) | |
|---|---|
| Omeprazole sodium | 93.5 weight % |
| Carboxymethylcellulose calcium | 3.7 weight % |
| Magnesium stearate | 1.9 weight % |

| Example 3 (capsules) | |
|---|---|
| Light silicic anhydride | 0.9 weight % |

The above ingredients are mixed thoroughly and filled into capsules in the conventional manner.

| Example 4 (injection) | |
|---|---|
| Omeprazole sodium | 40 mg |
| Sterile water to a final volume of | 10 ml |

The above ingredients are aseptically filled into separate vials to provide an injectable preparation.

| Example 5 (capsules) | |
|---|---|
| Pellets without an intermediate layer | |
| I Pulverized mannitol | 16150 g |
| Dehydrated lactose | 800 g |
| Hydroxypropylcellulose | 600 g |
| Microcrystalline cellulose | 400 g |
| II Omeprazole | 2000 g |
| Sodium laurylsulfate | 40 g |
| Disodium hydrogen phosphate | 80 g |
| Distilled water for injection | 4400 g |

The dry ingredients (I) are mechanically pre-mixed and, then, a granulated liquid component (II) containing omeprazole is added. The resulting mass is kneaded and moistened to a suitable viscosity. The wet mass is processed by means of an extruder to give spherical pellets which are then dried and screened for size selection.

| Intermediate-coated pellets | |
|---|---|
| Omeprazole pellets without an intermediate layer | 6000 g |
| III Hydroxypropylmethylcellulose | 240 g |
| Distilled water | 4800 g |

Using a fluidized-bed equipment, the polymer solution (III) is sprayed over the pellets without an intermediate layer. In this operation, the spray gun is positioned over the fluidized bed.

| Enteric-coated pellets | |
|---|---|
| Intermediate-coated pellets | 500 g |
| IV Hydroxypropylmethylcellulose phthalate | 57 g |
| Cetyl alcohol | 3 g |
| Acetone | 540 g |
| Ethanol | 231 g |

Using a fluidized-bed equipment, the polymer solution (IV) is sprayed over the intermediate-coated pellets using a spray gun positioned over the bed. After drying to a moisture content of 0.5%, the enteric-coated pellets are screened for size selection and filled in 225 mg portions into hard gelatin capsules (The above amount corresponds to 20 mg of omeprazole). Thirty capsules thus manufactured are packed into a tight container together with a desiccant.

We claim:
1. A method for the treatment of Campylobacter infections comprising administering to a patient suffering therefrom an amount of 5-methoxy-2-[[(4-methoxy-3,5-dimethyl-2-pyridinyl)methyl]-sulfinyl]-1H-benzimidazole or a pharmaceutically acceptable salt thereof sufficient for the treatment of said infection.

* * * * *